(12) United States Patent
Muntermann

(10) Patent No.: US 9,643,026 B2
(45) Date of Patent: May 9, 2017

(54) METHOD FOR COSMETIC SKIN SMOOTHENING AND DEVICE THEREFOR

(76) Inventor: Axel Muntermann, Wetzlar-Nauborn (DE)

( * ) Notice: Subject to any disclaimer, the term of this patent is extended or adjusted under 35 U.S.C. 154(b) by 234 days.

(21) Appl. No.: 13/517,302

(22) PCT Filed: Dec. 22, 2010

(86) PCT No.: PCT/EP2010/007855
§ 371 (c)(1),
(2), (4) Date: Aug. 28, 2012

(87) PCT Pub. No.: WO2011/076394
PCT Pub. Date: Jun. 30, 2011

(65) Prior Publication Data
US 2012/0310033 A1 Dec. 6, 2012

(30) Foreign Application Priority Data
Dec. 23, 2009 (DE) .................. 10 2009 060 543

(51) Int. Cl.
*A61N 2/02* (2006.01)
*A61N 2/04* (2006.01)
*A61N 2/00* (2006.01)

(52) U.S. Cl.
CPC .............. *A61N 2/004* (2013.01); *A61N 2/02* (2013.01)

(58) Field of Classification Search
CPC ............................................. A61N 2/00–2/12
USPC .................................. 600/9, 13, 14
See application file for complete search history.

(56) References Cited

U.S. PATENT DOCUMENTS

| | | | |
|---|---|---|---|
| 2003/0000646 A1 | 1/2003 | Ogino et al. | |
| 2003/0175234 A1* | 9/2003 | Hernandez | A61K 8/0208 424/74 |
| 2005/0228210 A1* | 10/2005 | Muntermann | 600/14 |
| 2007/0167517 A1* | 7/2007 | Kvitnitsky | A23L 1/302 514/474 |
| 2008/0139871 A1* | 6/2008 | Muntermann | 600/13 |
| 2008/0146865 A1* | 6/2008 | Muntermann | A61N 2/02 600/15 |
| 2009/0191291 A9* | 7/2009 | Ekker | 424/744 |
| 2009/0270945 A1* | 10/2009 | Markoll et al. | 607/50 |
| 2010/0042168 A1* | 2/2010 | Pasche et al. | 607/2 |

(Continued)

FOREIGN PATENT DOCUMENTS

| | | |
|---|---|---|
| DE | 19827736 A1 | 12/1999 |
| DE | 10002590 A1 | 8/2001 |
| DE | 10062050 A1 | 4/2002 |

(Continued)

OTHER PUBLICATIONS

"Related EP Patent Application No. 10 805 602.9 Office Action", Dec. 9, 2013, Publisher: EPo, Published in: EP.

(Continued)

*Primary Examiner* — Charles A Marmor, II
*Assistant Examiner* — Thaddeus Cox
(74) *Attorney, Agent, or Firm* — Kaplan Breyer Schwarz & Ottesen, LLP

(57) ABSTRACT

The invention relates to a method for cosmetic skin smoothening wherein two magnetic fields are generated perpendicular to each other and wherein the field strength of a quasi-static magnetic field or the frequency of an alternating magnetic field is modulated.

13 Claims, 9 Drawing Sheets

(56) References Cited

U.S. PATENT DOCUMENTS

2010/0179372 A1* 7/2010 Glassman .................. 600/9
2011/0130618 A1* 6/2011 Ron Edoute et al. .......... 600/14

FOREIGN PATENT DOCUMENTS

| DE | 102004006192 A1 | 9/2005 |
| EP | 1787678 A2 | 5/2007 |
| WO | WO 02092167 A1 * | 11/2002 |
| WO | 2005075019 A1 | 8/2005 |
| WO | 2009156117 A2 | 12/2009 |

OTHER PUBLICATIONS

Acquaviva, Laure, "PCT Application No. PCT/EP2010/007855 International Search Report Mar. 21, 2011", , Publisher: PCT, Published in: PCT.

* cited by examiner

METHOD FOR COSMETIC SKIN SMOOTHENING AND DEVICE THEREFOR

FIELD OF THE INVENTION

The invention relates to a method and a device for cosmetic skin smoothening, in particular using nuclear magnetic resonance.

BACKGROUND OF THE INVENTION

The invention relates to a cosmetic technique for skin smoothening, in particular for cellulite.

Cellulite presents as skin dimpling due to a quilt-shaped partitioning of subcutaneous fat. This does not constitute a disease; rather it is a biologically induced alteration of the connective tissue. Human skin is subject to various signs of ageing, e.g. wrinkling, slack skin as the connective tissue becomes thinner, etc. While these are normal signs of ageing, such alterations of the skin are extremely undesirable for a lot of people, and there have been a large variety of cosmetic and also chirurgical approaches for skin smoothening.

As for cellulite, in particular, attempts are made to stimulate circulation by lymph drainage and massage. Known approaches that employ technical devices, are a treatment with negative pressure in a vacuum tube, and acoustic wave therapy.

These known methods for skin smoothening are considerably expensive and annoying. Moreover, the obtainable result of the treatment is controversial.

OBJECT OF THE INVENTION

An object of the invention is to provide an effective cosmetic method for skin smoothening, in particular for cellulite.

In particular, the invention is intended to provide a method for skin smoothening which is easy to implement and free of detrimental side effects.

SUMMARY OF THE INVENTION

This object of the invention is already achieved by a method for cosmetic skin smoothening, a device for cosmetic skin treatment, and the use of nuclear magnetic resonance according to any of the independent claims.

Preferred embodiments and modifications of the invention are set forth in the respective dependent claims.

Accordingly, a method for cosmetic skin smoothening is provided which is in particular employed for slack skin and cellulite and wrinkles, especially in the face.

According to the method, a quasi-static magnetic field is generated in the zone of the skin area to be smoothened, and simultaneously an alternating magnetic field is generated perpendicular thereto.

By superpositioning the static field and the alternating magnetic field nuclear magnetic resonances can be obtained in the skin area to be treated.

Furthermore, the magnetic field strength of the quasi-static magnetic field and/or the frequency of the alternating magnetic field are modulated.

This modulation ensures in a fairly simple manner that resonance conditions are obtained in the entire skin area to be treated, at least temporarily, as will be described in more detail below.

The skin area to be treated is subjected to a substantially static magnetic field, resulting in an alignment of the spins in the tissue to be treated. An alternating magnetic field which is generally perpendicular to the static field induces the spins to turn, i.e. generates nuclear magnetic resonance.

Preferably, nuclear magnetic resonances are repeatedly generated, in particular via a so called fast adiabatic passage in which the amplitude of the "static" field is modulated, whereby nuclear magnetic resonance is generated in a large volume, in spite of inhomogeneities of the magnetic field, which allows to treat larger skin areas at once, such as e.g. the whole area of the face.

A fast adiabatic passage is known as an alteration of the frequency of the static field as slowly as to allow the magnetization to follow the orientation of the fluctuating field, but at the same time fast enough so that magnetization is not lost due to relaxation.

It will be understood that this illustration is based on a classical view of the nuclear magnetic resonance effect and that this ideal condition described only serves as an aid for explaining the effect to be considered statistically.

Apart from that, the use of nuclear magnetic resonance devices in medical applications is known above all as a diagnostic imaging method. However, such diagnostic devices work with higher field strengths, which are not an option for use in the cosmetic field, without medical assistance.

A quasi-static magnetic field in the sense of the invention is a magnetic field which aligns the spins according to the classical view. The denotation as a "quasi-static" field, however, does not exclude the field strength of this field to be modulated.

Furthermore, a device for generating nuclear magnetic resonances comprises a means for generating an alternating magnetic field which preferably is substantially perpendicular to the quasi-static magnetic field.

Especially to obtain a fast adiabatic passage, the field strength of the quasi-static magnetic field can be modulated with a modulation frequency $f_M$, in particular to obtain a fast adiabatic passage. Preferably, this modulation is linear resulting in a triangular signal. Other signal forms are contemplated, for example signal forms where the rise and/or decline of the field strength slow down midway between minimum and maximum.

Alternatively, the frequency of the alternating magnetic field can be modulated, instead of or besides the field strength of the quasi-static magnetic field, since the resonance condition depends on the field strength of the static magnetic field. However, it is preferred to modulate the field strength of the quasi-static magnetic field, as the technical implementation thereof is more easily achieved than frequency modulation of the alternating magnetic field.

In one embodiment of the invention, a cream is applied prior to and/or during the generation of the magnetic fields, which cream especially comprises at least one of the following components: water, hyaluronic acid, ubiquinone, collagen, and/or vitamin E. The substances mentioned are known for use in cosmetic skin treatment. In particular it is known that smoothening effects of the skin can be obtained by means of vitamin E, hyaluronic acid, and ubiquinone which is also known as Q11.

The inventor has found that the generation of nuclear magnetic resonances provides a synergic effect in the skin area to be treated which goes along with a significantly improved result. It is supposed by the inventor that this effect is due to a significantly improved absorbing capacity of the skin caused by nuclear magnetic resonance.

Moreover, the inventor has found that a significant treatment success is obtained especially with rather low field strengths of less than 50 gauss, preferably less than 30 gauss, and with rather low modulation frequencies $f_M$ of less than 100 Hz.

In particular, a modulation frequency between 1 and 50, preferably of 5 Hz±3 Hz, and more preferably of 5 Hz±2 Hz is suitable to achieve successful treatment.

The frequency of the alternating magnetic field, likewise, is rather low, and preferably is less than 100 kHz, and more preferably less than 50 kHz.

Surprisingly, the desired result is obtained which magnetic fields that are just not strong, skin smoothening is already obtained with small field strengths. Besides the surprising findings that strong fields do not yield improved results, this knowledge moreover enables to provide a device which is not dangerous, due to the weak fields that are generated, and which can be operated in cosmetic studios or by the user itself, without trained personal.

The devise that is used to perform the method, preferably has means for setting a modulation frequency $f_M$ of less than 100 Hz.

The inventor has found that the success of treatment significantly depends on the modulation frequency, with modulation frequencies below 100 Hz yielding significantly better treatment successes than higher frequencies.

Preferably, a modulation frequency $f_m$ is selected between 0.1 Hz and 100 Hz, more preferably between 2 Hz and 50 Hz.

Previously, it has been assumed that the modulation frequency only serves to obtain a fast adiabatic passage in the physical sense and that, if a fast adiabatic passage is obtained, treatment success does not depend on the modulation frequency.

In one embodiment of the invention, the means for setting a modulation frequency allows to set a plurality of substantially discrete frequencies, with a spacing of at least 1 Hz, preferably 2 Hz, and more preferably at least 5 Hz.

The inventor has found that in many cases different modulation frequencies are optimal.

The optimum modulation frequency for the respective indication such as skin type and pattern of wrinkles can be selected easily by a means for setting the modulation frequency.

To this end, the means for setting the modulation frequency may comprise a simple selection switch by means of which the treating person selects the indication.

Alternatively or in combination, the means for setting the modulation frequency comprises a card reader, e.g. a chip or magnetic card reader. The card may store a frequency pattern, treatment process, treatment duration, and/or other relevant parameters that are optimal for the respective indication.

For example, the inventor has found that a modulation frequency of about 5 Hz yields the best results of skin smoothening, in particular for cellulite.

The alternating magnetic field preferably has a frequency of less than 100 kHz, more preferably less than 50 kHz. The inventor has found that the treatment success significantly decreases at frequencies above 100 kHz.

Preferably, the device for generating nuclear magnetic resonances is adapted so that at least one of the following modulation frequencies can be selected:
5 Hz±2 Hz
10 Hz±3 Hz
20 Hz±5 Hz
40 Hz±5 Hz.

Surprisingly, the treatment success diminishes again at higher frequencies.

In one embodiment of the invention, the device comprises means for setting a sequence of at least two different modulation frequencies.

In a preferred embodiment of the invention, the device for generating the quasi-static magnetic field is adapted to obtain a field strength of less than 50 gauss, preferably less than 30 gauss. As already mentioned above, it has been found that low field strengths and hence low frequencies of the alternating magnetic field result in better treatment successes.

Furthermore, the field strengths are in a range so low as to allow the device according to the invention to be operated without trained personal.

The same applies to the transfer of energy generated by the device into the tissue to be treated, which is less than 1 mW/l, preferably less than 100 µW/l, and more preferably less than 10 µW/1. It has been found that the success of the treatment just not depend on a high energy input into the tissue to be treated. As the energy transfer induced by nuclear magnetic resonance is so low it is ensured that this cosmetic treatment does not entail any risk, neither for the client nor for the personal.

When the field strength of the quasi-static magnetic field is modulated, it is preferably modulated with an amount of at least 5%, preferably at least 10% and more preferably at least 15% of the minimum field strength of the quasi-static magnetic field. Thus, the quasi-static magnetic field consists of a basic amount which is increased by a modulation amount. A modulation of more than 5% of the basic amount is typically sufficient not only to compensate for inhomogenities of the field generated by the device itself within the tissue to be treated, but also to compensate for inhomogenities that are due to external magnetic fields which combine with the magnetic field of the device. This particularly applies to the terrestrial magnetic field, wherein, in a preferred embodiment of the invention, the field strength of the quasi-static magnetic field is modulated by twice, preferably by at least three times, and more preferably by at least six times the magnetic field strength of the terrestrial magnetic field.

The same principle may also be applied in an alternative embodiment of the invention in which the frequency of the alternating magnetic field can be modulated. Here, similarly, the alternating magnetic field can be modulated by an amount of at least 5%, preferably at least 10%, and more preferably at least 15% of the minimum frequency of the alternating magnetic field. To compensate for the terrestrial magnetic field, the modulation of the alternating magnetic field may be by at least 2 Hz, preferably at least 4 Hz, and more preferably at least 6 Hz.

In a preferred embodiment of the invention, the device is adapted so that a modulation frequency is chosen which results in a magnetization of at least 60%, preferably at least 70% of the maximum magnetization in the tissue to be treated. The term maximum magnetization is intended to designate the maximum achievable magnetization in the tissue to be treated for a respective field strength of the quasi-static field applied. With an ideal fast adiabatic passage, magnetization in the tissue to be treated approaches the value of maximum magnetization that is theoretically possible. The inventor has found that a minimum magnetization of about 60% should be provided and is sufficient to achieve successes in the smoothening of the skin.

In one embodiment of the invention, the frequency of the alternating magnetic field can be modulated by displacing plates of a condenser with respect to each other. The inventor has found that this presents a particularly simple technique to obtain a steady alteration of the frequency of the alternating magnetic field. Especially, in the preferred frequency ranges of the modulation frequency, motor-driven control of the condenser plates is possible.

Alternatively, the frequency of the alternating magnetic field can be modulated by switching condensers. However, such a construction is more complex in terms of circuitry, in particular when the device is operated at high voltages.

Additionally, the invention relates to a method of skin tightening using nuclear magnetic resonances in which nuclear magnetic resonances are generated in the tissue to be treated through a quasi-static magnetic field and an alternating magnetic field superimposed on the quasi-static magnetic field.

This includes periodically modulating the magnetic field strength of the quasi-static magnetic field and/or the frequency of the alternating magnetic field with a modulation frequency $f_M$, wherein a modulation frequency $f_M$ of less than 100 Hz is used for treatment.

As explained above, low modulation frequencies of less than 100 Hz, in particular modulation frequencies from 1 Hz to 50 Hz, yield surprising treatment successes.

Preferably, the duration of treatment is between one and 150 minutes, more preferably between 3 and 60 minutes, for one session.

The invention moreover relates to a device for cosmetic skin treatment which comprises means for generating a quasi-static magnetic field and means for generating an alternating magnetic field, and wherein the field strength of the static field and/or the frequency of the alternating magnetic field can be modulated with a modulation frequency $f_M$.

The device comprises a base and two angular side parts extending from the sides of the base, the means for generating the alternating magnetic field being arranged in the base, in particular in form of a coil, and the means for generating the quasi-static magnetic field being arranged in the side parts.

The means for generating the quasi-static magnetic field is formed such that the field lines extend from one of the side parts to the other one of the side parts, at least in portions thereof.

This is especially achieved by coils that are arranged in the side parts.

In contrast to conventional nuclear magnetic resonance imaging devices, the invention provides for a treatment device which opens opposite the base and which has a very large treatment zone that extends between the two side parts and in which nuclear magnetic resonances can be generated within a large volume.

Such a device is particularly useful for cosmetic applications, as the patient does not have to be introduced into a tube.

Rather, the device for generating nuclear magnetic resonances can be formed as a module which for example is a part of an adjustable treatment chair for the treatment of the face, or which e.g. in a slightly smaller embodiment can be attached directly to the client, e.g. at his or her arm or leg, by a textile strip.

The invention moreover relates to the use of nuclear magnetic resonance for cosmetic skin smoothening, in particular for cellulite.

BRIEF DESCRIPTION OF THE DRAWINGS

The invention will now be described in detail with reference to the drawings of FIG. 1 to FIG. 5 which show schematically illustrated embodiments of the invention.

DETAILED DESCRIPTION OF THE DRAWINGS

Figure 1:
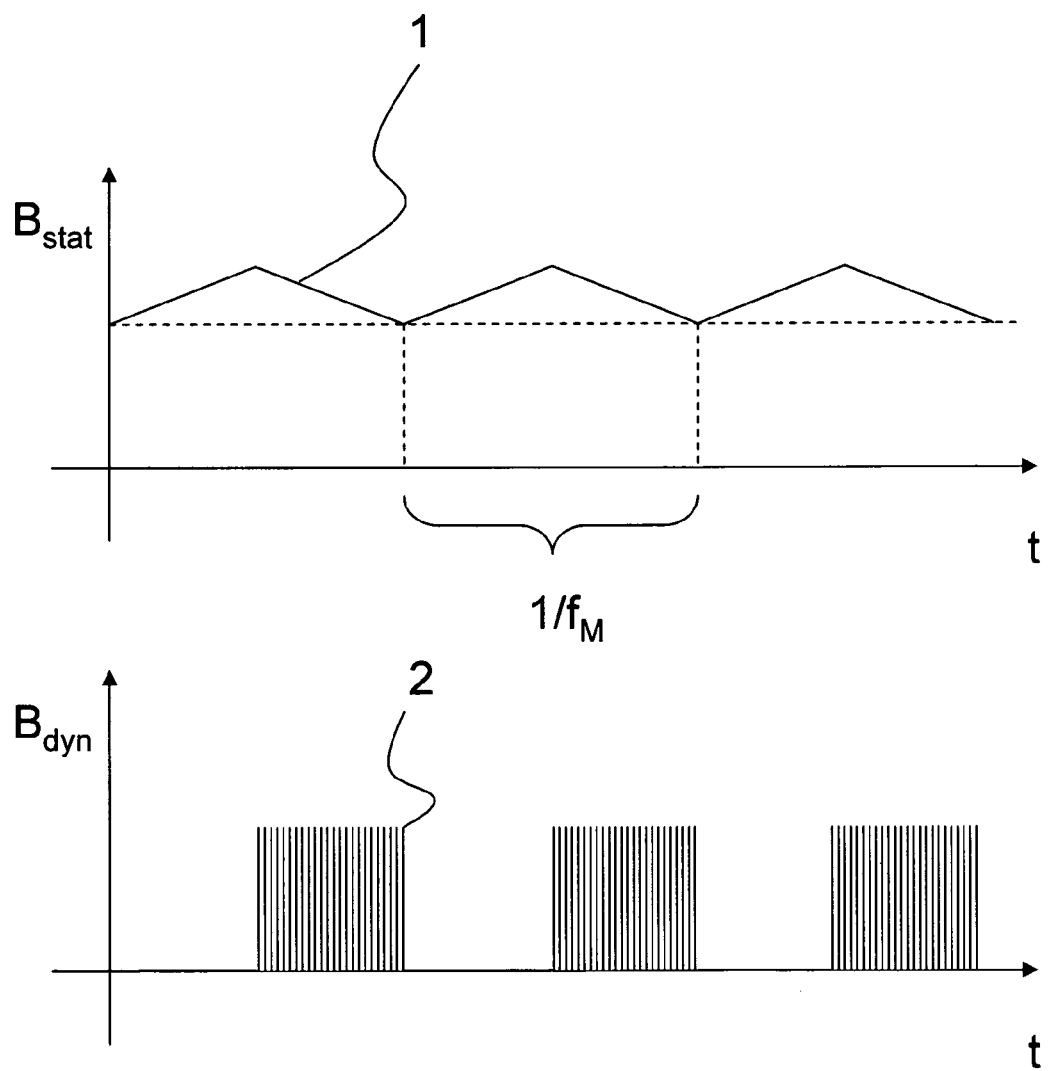
FIG. 1 schematically shows the field strengths of the two magnetic fields in an embodiment in which the quasi-static magnetic field is modulated.

In FIG. 1, the upper graph shows the static magnetic field plotted against time, and the lower graph shows the alternating magnetic field plotted against time.

It can be seen that the field strength of the quasi-static magnetic field 1 comprises a basic amount which is indicated by the dotted line. Beyond the basic amount, the magnetic field strength of the quasi-static magnetic field 1 is modulated with a triangular signal, resulting in a linear rise and decline of the field. A complete pass, that is to say a rise followed by a decline to the amplitude of the basic amount, corresponds to 1 $f_M$.

To obtain a fast adiabatic passage, an alternating magnetic field is switched on during each drop of the static magnetic field. The field strength of the alternating magnetic field 2 which in the present embodiment is a sinusoidal field (not shown) does not change substantially. Rather, due to switching on and off essentially a square wave signal is provided. Other signal patterns are contemplated as well.

During the decline of the field strength of the quasi-static field 1 nuclear magnetic resonance is generated in the tissue to be treated.

Figure 2:
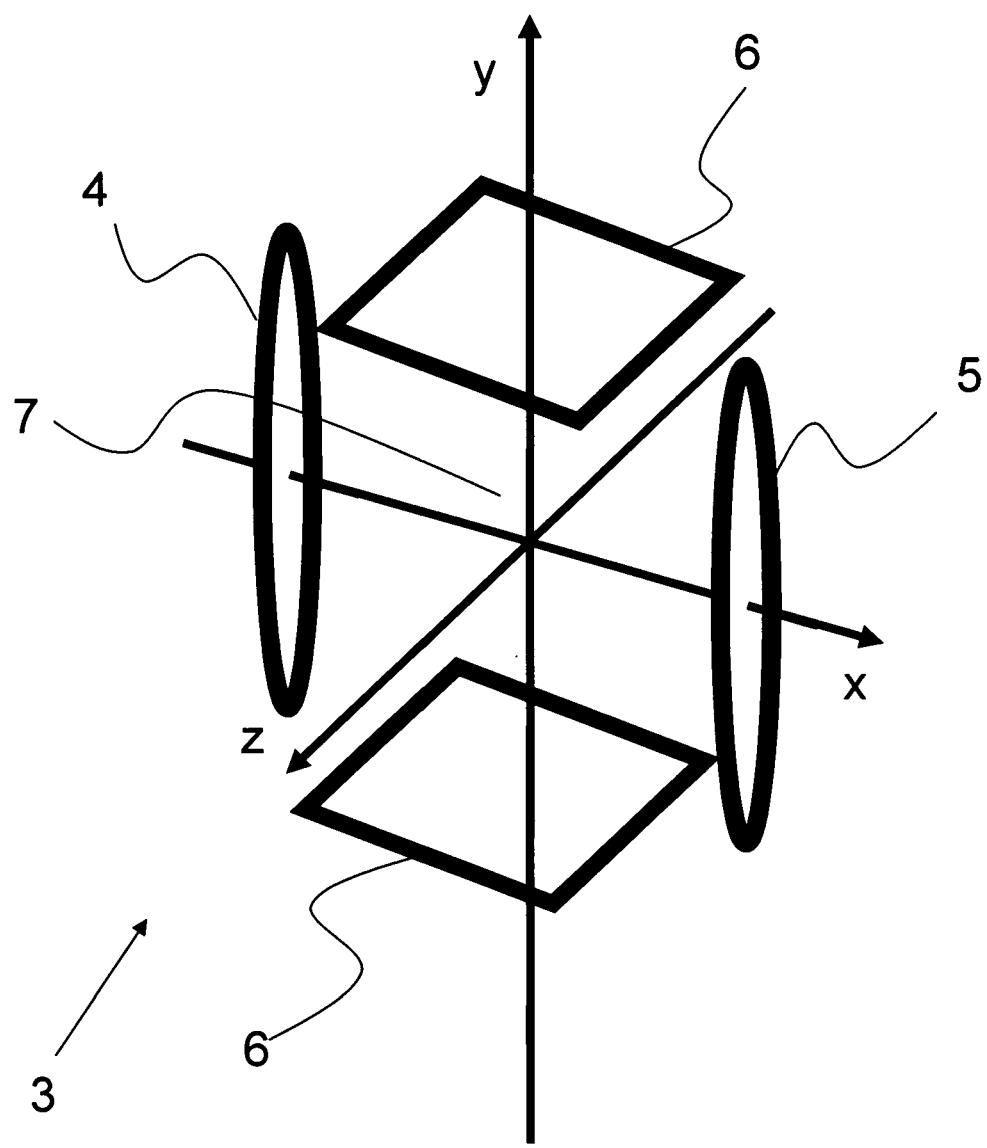
FIG. 2 schematically shows the salient components of a device for generating nuclear magnetic resonances.

With reference to FIG. 2, the salient components of a first device 3 for generating nuclear magnetic resonances shall be described.

The device comprises means 6 for generating a quasi-static field which in this embodiment include permanent magnets and a coil (not illustrated). In this case, the permanent magnet may generate the basic field whereas the coil provides for the modulation of the field strength.

The means 6 for generating the quasi-static field generates a field as homogenous as possible within the treatment zone 7 in the direction of the y-axis.

Furthermore, the device 3 for cosmetic skin smoothening comprises coils 4 and 5 which can be used to generate an alternating magnetic field in the direction of the x-axis.

Thus, the alternating magnetic field is superimposed on the quasi-static magnetic field and is perpendicular thereto which allows nuclear magnetic resonances to be produced in the tissue to be treated.

Figure 3:
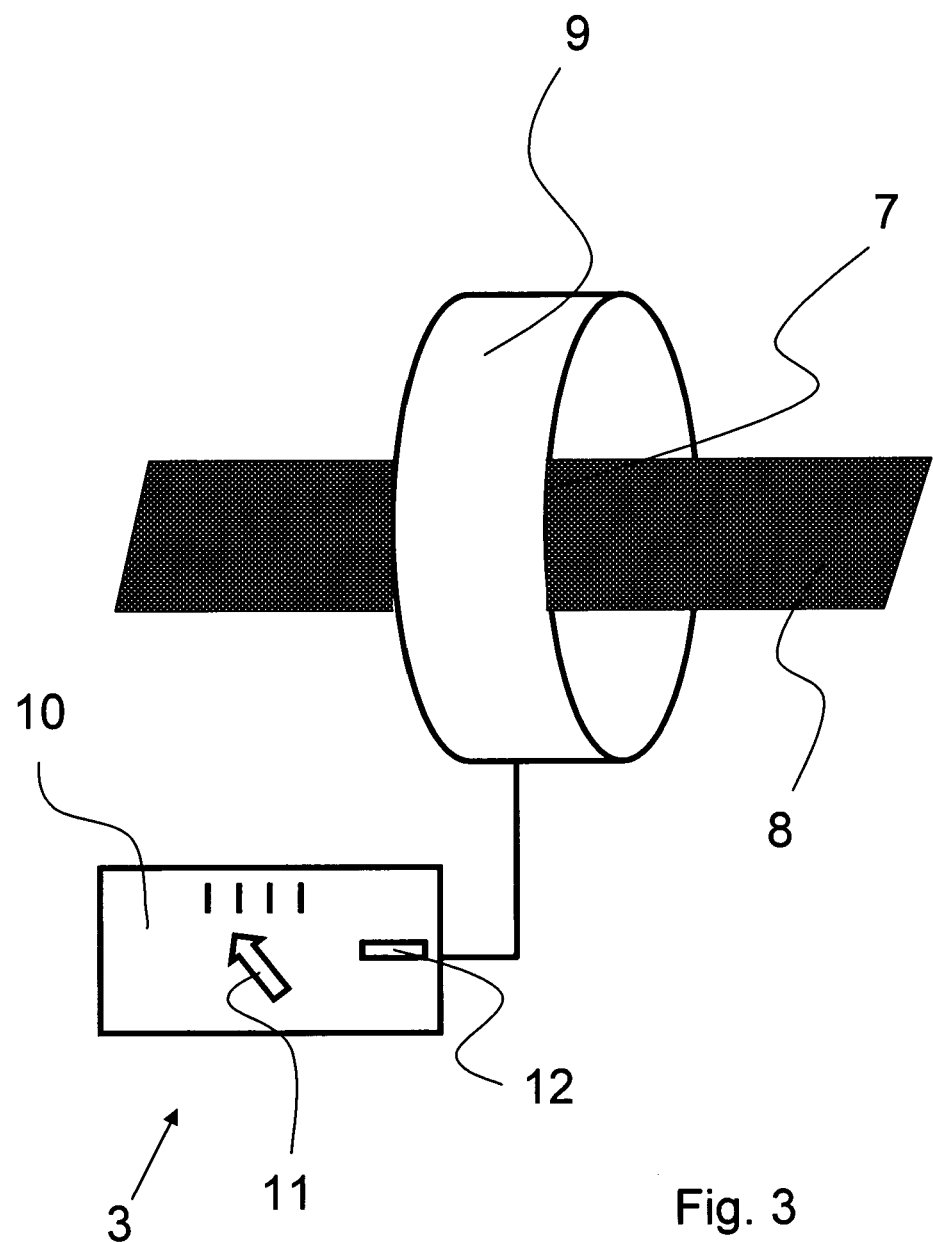
FIG. 3 schematically shows an arrangement comprising a device for generating nuclear magnetic resonances.

FIG. 3 schematically shows a device 3 for generating nuclear magnetic resonances. The device comprises an annular tube 9 which includes the coils illustrated in FIG. 2.

The means for generating the quasi-static field is not explicitly illustrated in this exemplary embodiment.

A treatment zone 7 is arranged within annular tube 9. During treatment, the client (not shown) rests upon a couch 8, which extends through annular tube 9.

The device moreover comprises a control means 10 which serves to control the coils (not shown) provided in the annular tube. The control means 10 on the one hand comprises a selection switch 11 to easily select different modulation frequencies.

Additionally, the control means 10 of this exemplary embodiment comprises a card reader 12. The card reader 12 allows treatment frequencies and other relevant parameters that are stored on a chip or magnetic card to be read and so, likewise, to be easily selected by the client.

Figure 4:
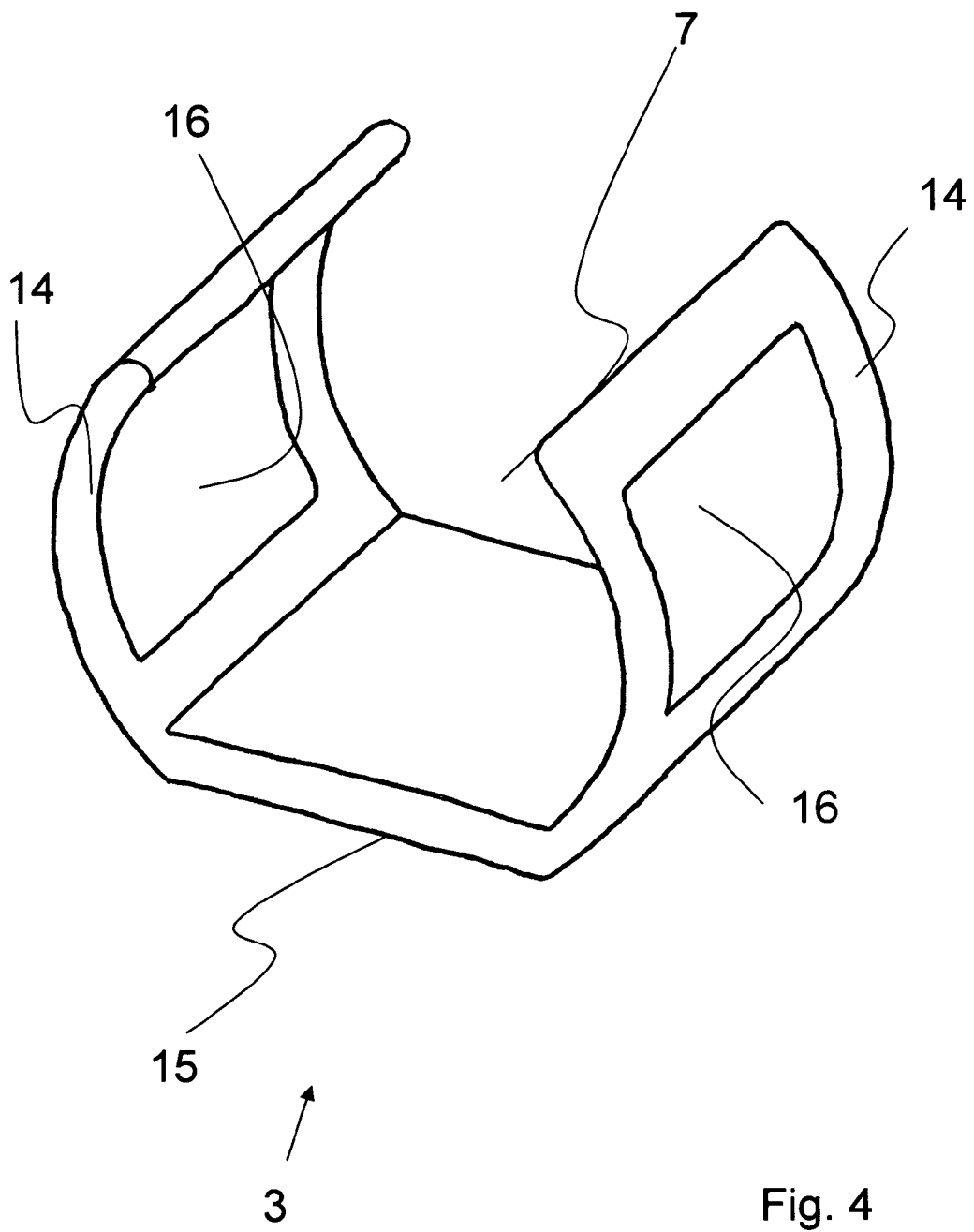
FIGS. 4 and 5 schematically show an alternative device for generating nuclear magnetic resonances.

FIG. 4 schematically illustrates a device 3 for generating nuclear magnetic resonances which is especially suitable for cosmetic purposes in this embodiment.

The device 3 comprises a base 15 which for example serves as a rest for the client's head.

Two side parts 14 extend from base 15.

Side parts 14 have a curved shape, in a front view, and an approximately circle segment-shaped or U-shaped cross section.

Furthermore, the two side parts 14 form a frame and so each have a recess 16.

Device 3 is open opposite base 15 which provides for significantly better accessibility of the treatment zone 7 provided between side parts 14 and base 15.

A first means for generating an alternating magnetic field is provided in base 15 (not shown).

In one embodiment, the means for generating nuclear magnetic resonances is dimensioned for the treatment of the facial skin of the client.

However it is also contemplated to use smaller dimensioned devices, for example for the treatment of the skin on arms and legs. In this case, the device as illustrated may be fixed to the arm or leg of the client, for example using straps, in particular velcro straps. An attachment to a treatment chair is also possible.

Figure 5:
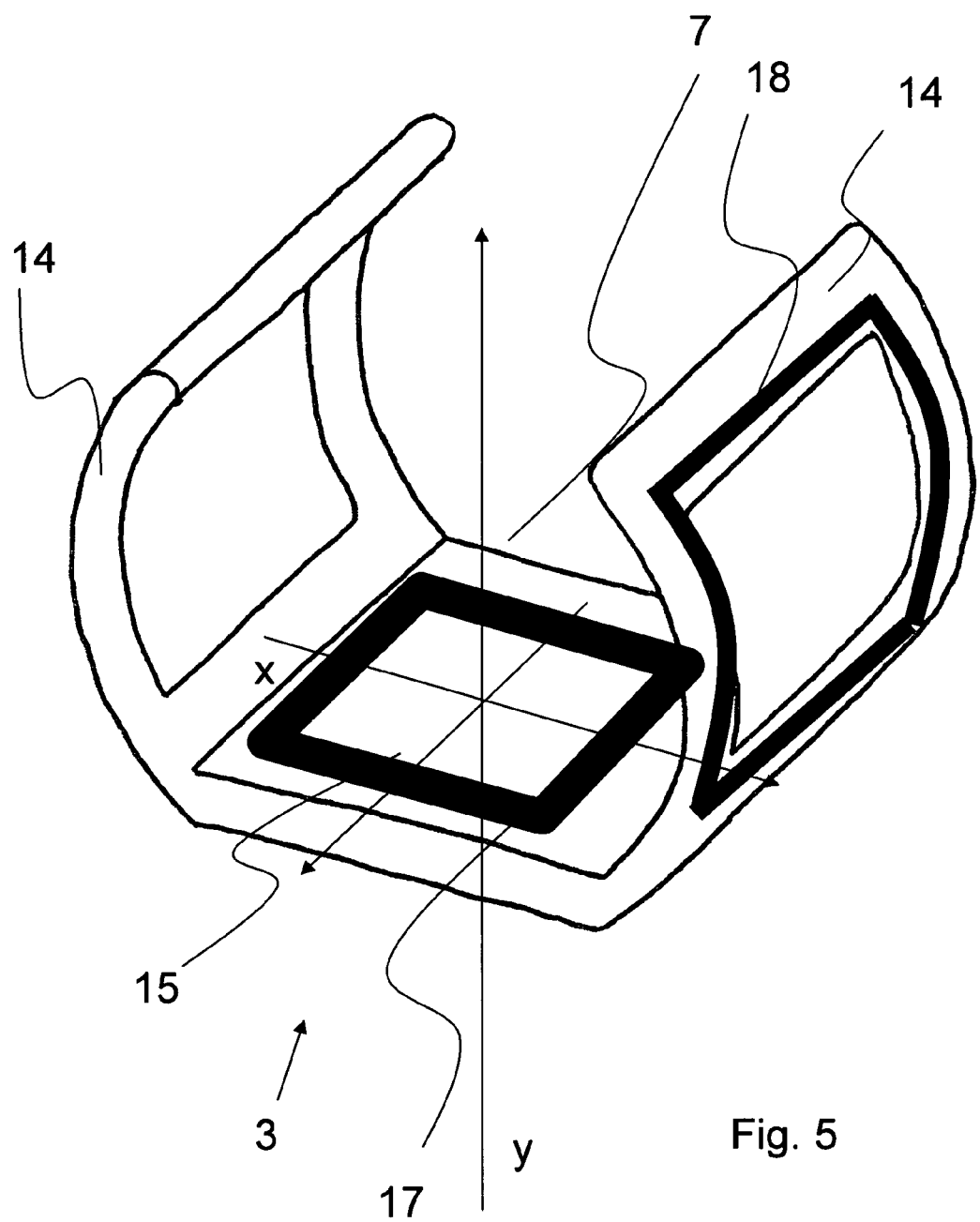

FIG. 5 shows the embodiment of a device according to FIG. 4 for generating nuclear magnetic resonances, with a coil 17 schematically drawn as included in base 15 of this embodiment, which coil provides a means for generating an alternating magnetic field in this exemplary embodiment.

A coil 18 is provided in each of the side parts 14 which can be used to produce a magnetic field. The coil in the left hand side part is not shown, but it will be understood that a magnetic field can be generated using the coils in the side parts 14 which is substantially perpendicular to the magnetic field generated by coil 17, within the treatment zone 7.

The coils can be powered via a mains-independent control device, in particular one that includes an accumulator (not shown).

Thus, nuclear magnetic resonances can be generated within the treatment zone 7 in the skin area to be treated (not shown).

A first magnetic field is produced using coil 17 incorporated in base 15, with field lines that extend substantially along the y-axis, in the treatment zone.

The coils in the side parts 14 generate a field perpendicular thereto, with field lines that extend substantially along the x-axis. Thus, the coils in the side parts 14 form a second means for generating a substantially static magnetic field. The generated field is very homogeneous, due to the arrangement that is close to that of a Helmholtz coil.

Thus, for producing nuclear magnetic resonances in the tissue to be treated it is advantageous to produce a substantially static magnetic field using the coils arranged in the side parts 14, and to produce an alternating field perpendicular thereto which causes the spins to turn, using coil 17.

Figure 6:
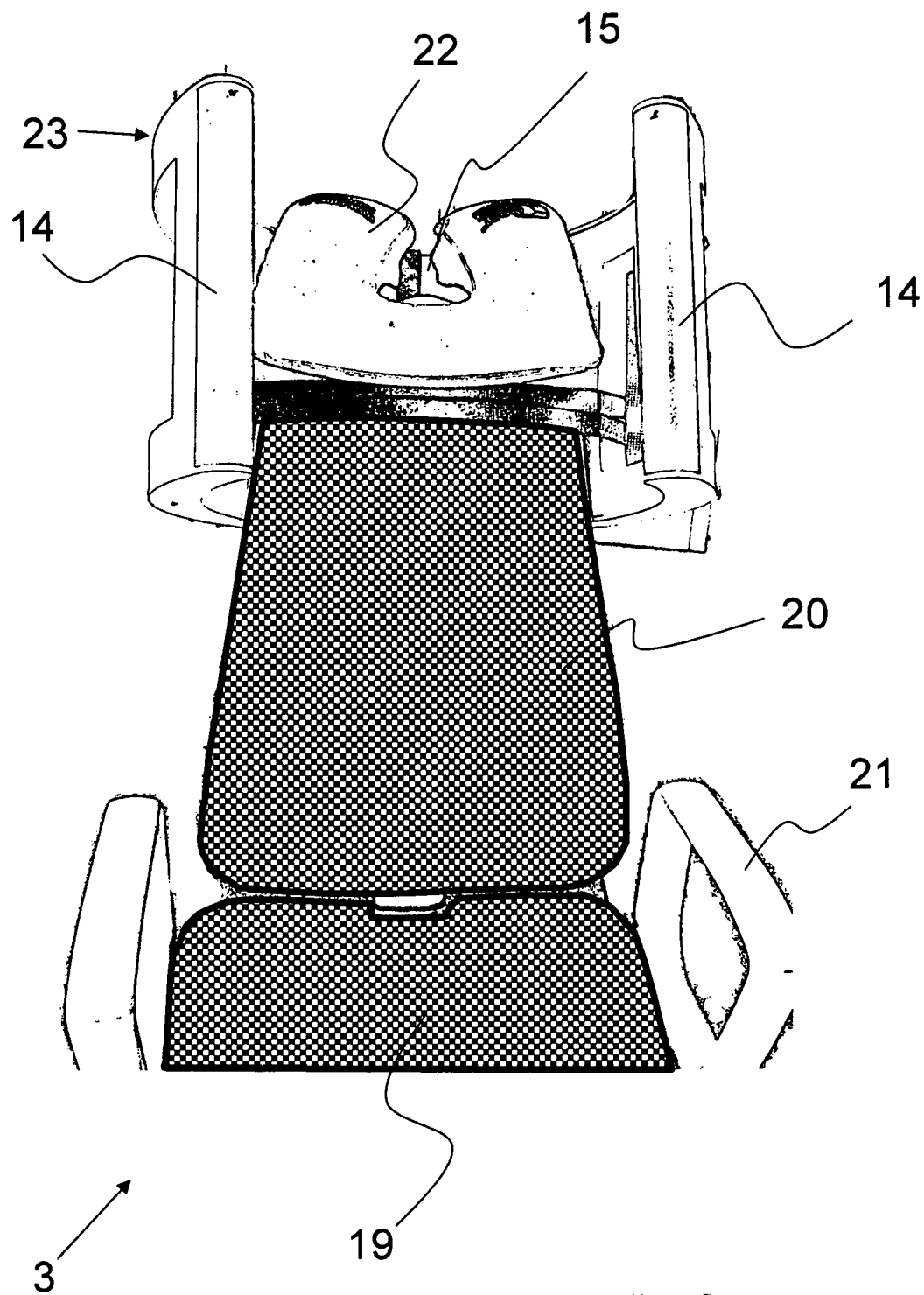
FIG. 6 shows the device for generating nuclear magnetic resonances as illustrated in FIGS. 4 and 5, mounted to a treatment chair.

FIG. 6 schematically illustrates another embodiment of the invention in which the device 3 for generating nuclear magnetic resonances comprises a seat 19 on which a client may sit. To enhance comfort, the device additionally comprises a backrest 20, an armrest 21, and a neck support 22.

A module 23 which comprises base 15 and side parts 14 is disposed essentially vertically.

Preferably, module 23 is adjustable, at least in height, so that the device can be adjusted to different sizes, or to treat different skin portions.

Preferably, the treatment chair including seat 19 and backrest 20 is further equipped with an adjustable legrest (not shown), and is designed to be adjustable in various ways, in particular adjustable in height, with an adjustable backrest and adjustable armrests.

Figure 7:
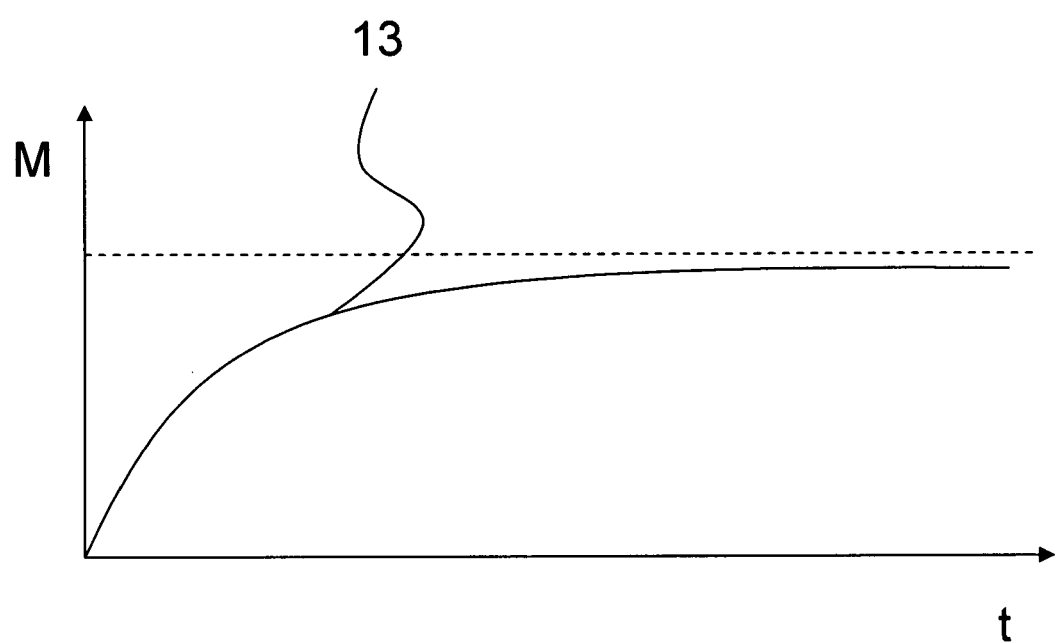
FIG. 7 shows the process of magnetization in the tissue to be treated.

Referring to FIG. 7, magnetization 13 in the skin area to be treated will now be described schematically. The rate at which the spins react with its neighbors depends on the lattice. With a fast adiabatic passage a maximum magnetization of the tissue to be treated can be yielded, which in this case is indicated by a dotted line. In reality this maximum value cannot be achieved entirely; rather relative magnetization of the tissue approximates the maximum value. By altering the modulation frequency, among others, magnetization more or less approaches this maximum value. The inventor has found that a magnetization of about 60% is sufficient to obtain significant smoothening effects.

Figure 8:
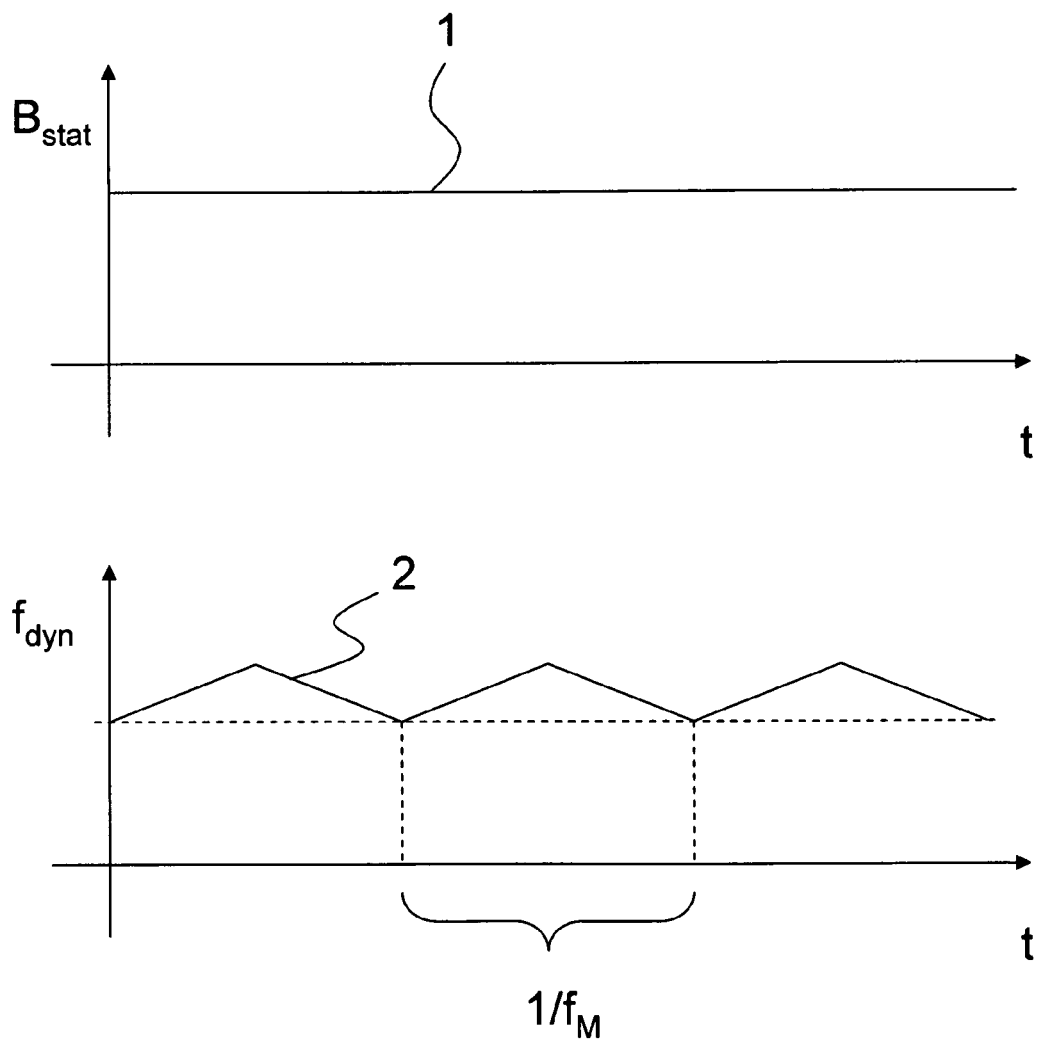
FIG. 8 shows the behavior of the static magnetic field and the frequency of the alternating magnetic field of an alternative embodiment of the invention in which the frequency of the alternating magnetic field is modulated.

With reference to FIG. 8, an alternative embodiment of the invention is described in which the frequency of the alternating magnetic field is modulated.

In this exemplary embodiment, the field strength of the illustrated static magnetic field 1 is constant.

Below, the frequency of the alternating magnetic field 2 is illustrated which is modulated as a triangular signal. Here likewise, a complete pass corresponds to 1 $f_M$. A modulation of the alternating magnetic field has the same physical results as a modulation of the quasi-static field. The modulation of the frequency of the alternating field provides for a fast adiabatic passage in the area to be treated.

Figure 9:
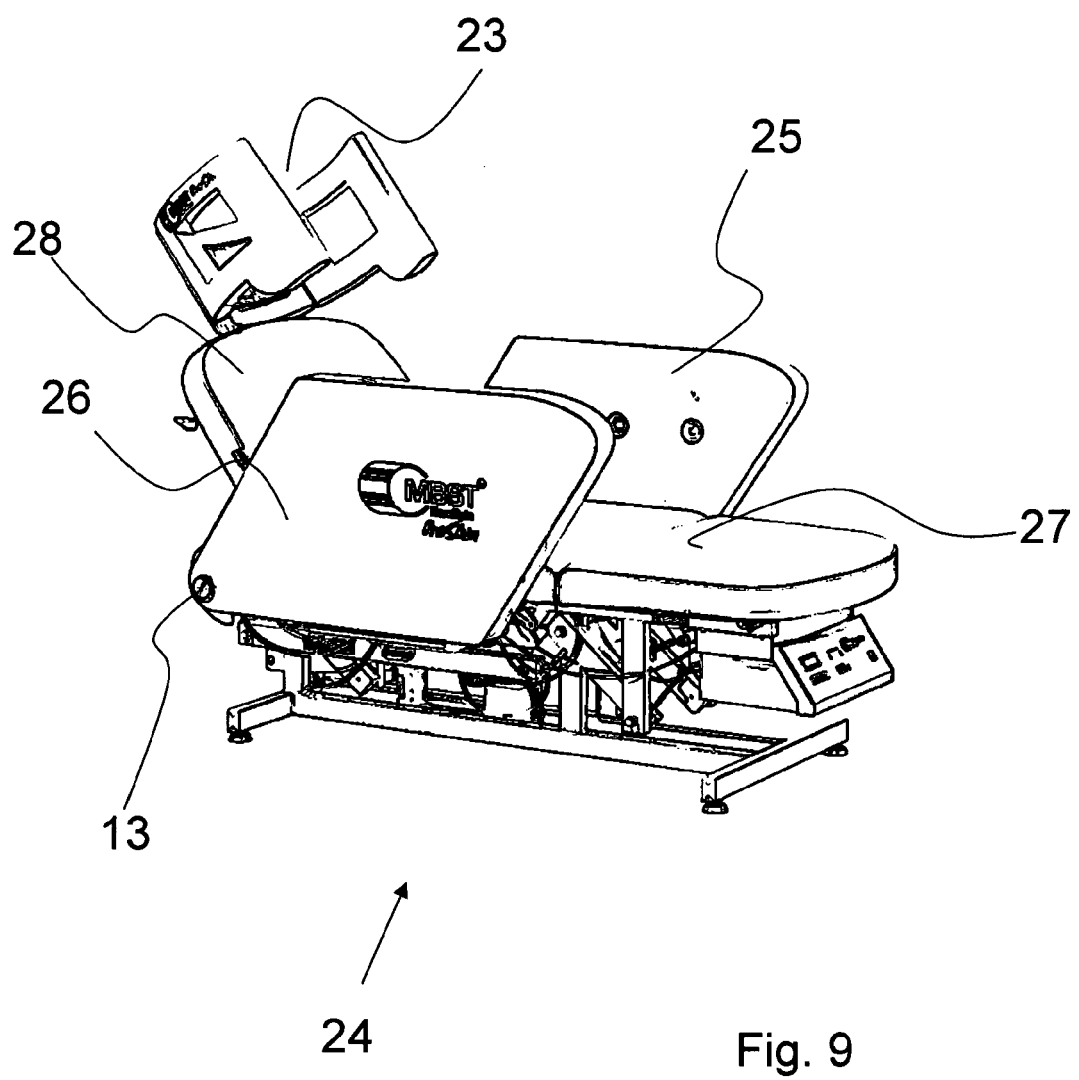
FIG. 9 shows another alternative device for generating nuclear magnetic resonances.

FIG. 9 shows another embodiment of a device 24 for generating nuclear magnetic resonances.

The device 24 for generating nuclear magnetic resonances in this exemplary embodiment comprises a motor-driven adjustable couch 27 with a backrest 28 which not only allows the client to lie but also to sit in an upright or half-upright position.

This device 24 for generating nuclear magnetic resonances comprises two treatment zones.

To this end, two side parts 25, 26 are provided which extend along couch 27. Each of the side parts has incorporated a coil (not shown). Using the coils included in side parts 25, 26, a substantially static magnetic field can be generated which extends from one of the side parts to the other one. Below couch 27 a coil (not shown) is arranged for generating an alternating magnetic field which extends substantially perpendicular to the static magnetic field, between side parts 25 and 26. Thus, a first treatment zone is provided between side parts 25 and 26. To provide for a better access, at least one of the side parts 25, 26 is mounted to a pivot joint 13 and can be pivoted sideways towards rest 28.

In the head zone, another device for generating magnetic fields is arranged in form of a module 23. This module 23 is used to treat the facial skin. The configuration of the coils corresponds to the coil configuration described in conjunction with FIG. 6.

So, the device 24 for generating nuclear magnetic resonances illustrated in FIG. 9 can be used to treat the skin of the client in two treatment zones. The treatments may be performed independently from each other; in particular, the static field produced by module 23 can be swept using a different frequency.

It will be understood that the invention is not limited to a combination of features as described above; rather a person skilled in the art will combine any features as far as appropriate.

LIST OF REFERENCE NUMERALS

1 field strength of quasi-static magnetic field
2 field strength of alternating magnetic field
3 device for generating nuclear magnetic resonances
4 coil
5 coil
6 means for generating a quasi-static field
7 treatment zone
8 couch
9 annular tube
10 control means
11 selection switch
12 card reader
13 relative magnetization of the skin area
14 side part
15 base
16 recess
17 coil
18 coil
19 seat
20 backrest
21 armrest
22 neck support
23 module
24 device for generating nuclear magnetic resonances
25 side part
26 side part
27 couch
28 backrest

What is claimed is:

1. A method for cosmetic skin smoothening comprising the steps of:
    generating, by a first side part or a second side part of a device, a quasi-static magnetic field in a zone of a skin area to be smoothened, wherein the quasi-static magnetic field is generated by a first coil or a second coil respectively arranged in the first and second side parts, with each side part having an angular cross section for accommodating a head of a patient, and wherein generating the quasi-static magnetic field includes generating a magnetic field with field lines that extend from one of the side parts to the other one of the side parts, at least in portions thereof,
    simultaneously generating, by a base of the device, an alternating magnetic field in the zone of the skin area to be smoothened, wherein the alternating magnetic field is generated perpendicular to said quasi-static magnetic field, at least in portions thereof, by a third coil arranged in the base, and wherein the first and the second side parts extend from sides of the base to form a module,
    modulating a field strength of the quasi-static magnetic field or a frequency of the alternating magnetic field,
    wherein modulating the field strength of the quasi-static magnetic field or the frequency of the alternating magnetic field causes a fast adiabatic passage in a tissue to be treated,
    wherein the modulation frequency is selected so that magnetization is at least 60% of a maximum magnetization in the tissue to be treated, and
    wherein a cream is applied during the generation of the quasi-static magnetic field and the alternating magnetic field, which cream comprises hyaluronic acid.

2. The method for cosmetic skin smoothening according to claim 1, wherein the field strength of the quasi-static magnetic field or the frequency of the alternating magnetic field is modulated with a modulation frequency $f_M$, wherein said modulation frequency $f_M$ is less than 100 Hz.

3. The method for cosmetic skin smoothening according to claim 1, wherein a modulation frequency $f_M$ is set between 0.1 Hz and 100 Hz.

4. The method for cosmetic skin smoothening according to claim 1, wherein the field strength of the quasi-static magnetic field is set to be less than 50 gauss.

5. The method for cosmetic skin smoothening according to claim 1, wherein the frequency of the alternating magnetic field is less than 100 kHz.

6. The method for cosmetic skin smoothening according to claim 1, wherein at least two different modulation frequencies are used during treatment.

7. The method for cosmetic skin smoothening according to claim 1, wherein the modulation of the field strength of the quasi-static magnetic field is by at least 5% of an amplitude of a minimum field strength of the quasi-static magnetic field.

8. The method for cosmetic skin smoothening according to claim 1, wherein the modulation of the frequency of the alternating magnetic field is by at least 5% of a minimum frequency of the alternating magnetic field.

9. The method for cosmetic skin smoothening according to claim 1, wherein the modulation of the field strength of the quasi-static magnetic field is by at least twice of the magnetic field strength of a terrestrial magnetic field.

10. The method for cosmetic skin smoothening according to claim 1, wherein a duration of treatment is from 1 to 150 min.

11. A device for cosmetic skin treatment, comprising:
    a first side part arranged with a first coil and a second side part arranged with a second coil for generating a quasi-static magnetic field, with each side part having an angular cross section for accommodating a head of a patient;
    a base arranged with a third coil for generating an alternating magnetic field;
    wherein the first and second side parts extend from sides of the base to form a module,
    wherein the alternating magnetic field is generated generally perpendicular to the quasi-static magnetic field, at least in portions thereof;
    wherein a field strength of the quasi-static magnetic field can be modulated with a modulation frequency $f_M$;
    wherein the field strength of the quasi-static magnetic field causes a fast adiabatic passage in the tissue to be treated;
    wherein the modulation frequency is selected so that magnetization is at least 60% of a maximum magnetization in a tissue to be treated;
    wherein one cycle of rising and declining of the field strength of the quasi-magnetic field corresponds to $1/f_M$;

wherein generating the quasi-static magnetic field includes generating a magnetic field with field lines that extend from one of the side parts to the other one of the side parts, at least in portions thereof; and wherein the device comprises means for setting a sequence of at least two different discrete modulation frequencies with a spacing of at least 5 Hz.

12. The device for cosmetic skin treatment according to claim 11, wherein the device opens opposite the base.

13. The device for cosmetic skin treatment according to claim 12, wherein the device comprises an adjustable chair.

* * * * *